United States Patent
Delgado et al.

(10) Patent No.: US 9,244,368 B2
(45) Date of Patent: Jan. 26, 2016

(54) PARTICLE CONTROL NEAR RETICLE AND OPTICS USING SHOWERHEAD

(71) Applicants: Gildardo R. Delgado, Livermore, CA (US); Frank Chilese, San Ramon, CA (US); Rudy Garcia, Union City, CA (US); John R. Torczynski, Albuquerque, NM (US); Anthony S. Geller, Albuquerque, NM (US); Daniel J. Rader, Albuquerque, NM (US); Leonard E. Klebanoff, Dublin, CA (US); Michail A. Gallis, Albuquerque, NM (US)

(72) Inventors: Gildardo R. Delgado, Livermore, CA (US); Frank Chilese, San Ramon, CA (US); Rudy Garcia, Union City, CA (US); John R. Torczynski, Albuquerque, NM (US); Anthony S. Geller, Albuquerque, NM (US); Daniel J. Rader, Albuquerque, NM (US); Leonard E. Klebanoff, Dublin, CA (US); Michail A. Gallis, Albuquerque, NM (US)

(73) Assignees: KLA-Tencor Corporation, Milpitas, CA (US); Sandia Corporation, Albuquerque, NM (US)

( * ) Notice: Subject to any disclaimer, the term of this patent is extended or adjusted under 35 U.S.C. 154(b) by 295 days.

(21) Appl. No.: 14/033,929

(22) Filed: Sep. 23, 2013

(65) Prior Publication Data

US 2014/0085618 A1 Mar. 27, 2014

Related U.S. Application Data

(60) Provisional application No. 61/706,070, filed on Sep. 26, 2012.

(51) Int. Cl.
*G03B 27/52* (2006.01)
*G03B 27/54* (2006.01)
(Continued)

(52) U.S. Cl.
CPC .......... *G03F 7/70841* (2013.01); *G03F 1/0092* (2013.01); *G03F 7/70916* (2013.01); *G03F 7/70933* (2013.01)

(58) Field of Classification Search
CPC ... G03F 1/0092; G03F 7/70591; G03F 7/708; G03F 7/70841; G03F 7/70858; G03F 7/70866; G03F 7/70908; G03F 7/70916; G03F 7/70933
USPC ...................................... 355/30, 67
See application file for complete search history.

(56) References Cited

U.S. PATENT DOCUMENTS 6,445,439 B1    9/2002    McCullough
7,030,959 B2    4/2006    Sogard
(Continued)

FOREIGN PATENT DOCUMENTS

KR    20010067473    7/2001
KR    20090092712    1/2009
(Continued)

OTHER PUBLICATIONS

Yook Se-Jin et al. "Experimental Investigations of Protection Schemes for Extreme Ultraviolet Lithography Masks in Carrier Systems Against Horizontal Aerosol Flow." vol. 20, pp. 176-186.
(Continued)

*Primary Examiner* — Colin Kreutzer
(74) *Attorney, Agent, or Firm* — Simpson & Simpson, PLLC (57) ABSTRACT

A method and an apparatus to protect a reticle against particles and chemicals in an actinic EUV reticle inspection tool are presented. The method and apparatus utilizes a pair of porous metal diffusers in the form of showerheads to provide a continual flow of clean gas. The main showerhead bathes the reticle surface to be inspected in smoothly flowing, low pressure gas, isolating it from particles coming from surrounding volumes. The secondary showerhead faces away from the reticle and toward the EUV illumination and projection optics, supplying them with purge gas while at the same time creating a buffer zone that is kept free of any particle contamination originating from those optics.

16 Claims, 6 Drawing Sheets

(51) Int. Cl.
*G03F 7/20* (2006.01)
*G03F 1/00* (2012.01)

(56) References Cited

U.S. PATENT DOCUMENTS

| | | | |
|---|---|---|---|
| 7,718,004 | B2 | 5/2010 | Fukasawa et al. |
| 7,812,329 | B2 | 10/2010 | Brandt et al. |
| 7,875,864 | B2 | 1/2011 | Sogard |
| 8,149,386 | B2 | 4/2012 | Kajiyama |
| 2007/0209226 | A1* | 9/2007 | Coon .................. G03F 7/70875 34/403 |
| 2008/0184584 | A1 | 8/2008 | Sogard |
| 2011/0198034 | A1 | 8/2011 | Duan et al. |
| 2012/0067971 | A1 | 3/2012 | Byun et al. |

FOREIGN PATENT DOCUMENTS

| | | |
|---|---|---|
| WO | 2006122578 A1 | 11/2006 |
| WO | 2011134692 | 11/2011 |
| WO | 2012054200 A3 | 6/2012 |

OTHER PUBLICATIONS

Moors Roel et al. "Electrostatic mask protection for extreme ultraviolet lithography." vol. 20 http://ieeexplore.ieee.org/Xplore/defdeny.jsp?url=http%3A%2F%2Fieeexplore.ieee.org%2Fstamp%2Fstamp.jsp%3Ftp%3D%26arnumber%3D4972302%26userType%3Dinst&denyReason=-133&arnumber=4972302&productsMatched=null&userType=inst.

Daniel J. Radera & Anthony S. Gellera. "Showerhead-Enhanced Inertial Particle Deposition in Parallel-Plate Reactors." vol. 28, pp. 105-132. http://www.tandfonline.com/doi/abs/10.1080/02786829808965515#preview.

Bird, 1994: G. A. Bird, Molecular Gas Dynamics and the Direct Simulation of Gas Flows, Clarendon Press, Oxford, UK, 1994; updated, 1998.

Comsol, 2008: Comsol AB, Comsol Multiphysics User's Guide, Version 3.5a, COMSOL AB, Stockholm, Sweden, 2008; http://www.comsol.com/, 2012.

Gallis et al., 2001: M. A. Gallis, J. R. Torczynski, and D. J. Rader, "An Approach for Simulating the Transport of Spherical Particles in a Rarefied Gas Flow via the Direct Simulation Monte Carlo Method," Physics of Fluids, vol. 13, No. 11, pp. 3482-3492, 2001.

Gallis et al., 2008a: M. A. Gallis, J. R. Torczynski, and D. J. Rader, "Nonzero-Concentration Boundary Condition for Advection-Diffusion Aerosol-Transport Modeling," Aerosol Science and Technology, vol. 42, pp. 829-831, 2008.

Gallis et al., 2008b: M. A. Gallis, J. R. Torczynski, and D. J. Rader, "Nanoparticle Knudsen Layers in Gas-Filled Microscale Geometries," Physical Review E, vol. 77, paper 036302, 2008.

Gallis et al., 2012: M. A. Gallis and J. R. Torczynski, "Direct Simulation Monte Carlo-Based Expressions for the Gas Mass Flow Rate and Pressure Profile in a Microscale Tube," Physics of Fluids, vol. 24, No. 1, paper 012005, 2012.

Ho and Webb, 2006: C. K. Ho and S. W. Webb, Gas Transport in Porous Media, Springer, Dordrecht, The Netherlands, 2006, especially Part 1, Section 2.

Klinkenburg, 1941: L. J. Klinkenberg, "The Permeability of Porous Media to Liquids and Gases," API Drilling Production and Practice, pp. 200-213, 1941.

Mott, 2012: Mott Corporation, http://lwww.mottcorp.com/, "Porous Metal Overview," http://www.mottcorp.com/media/media_overview.cfm/, 2012.

Oldenburg et al., 2004: C. M. Oldenburg, S. W. Webb, K. Pruess, and G. J. Moridis, "Mixing of Stably Stratified Gases in Subsurface Reservoirs: A Comparison of Diffusion Models," Transport in Porous Media, vol. 54, pp. 323-334, 2004.

Reid et al., 1987: R. C. Reid, J. M. Prausnitz, and B. E. Poling, The Properties of Gases and Liquids, fourth edition, McGraw-Hill Book Company, New York, NY, 1987.

Torczynski, "Particle Contamination Analysis for Reticles in Carrier Inner Pods," SPIE paper 69213G, edited by F. M. Schellenberg, Proceedings of SPIE, vol. 6921, paper 69213G, pp. 1-11, 2008.

Torczynskii et al., 2011: J. R. Torczynski and M. A. Gallis, "DSMC-Based Shear-StressNelocity-Slip Boundary Condition for Navier-Stokes Couette-Flow Simulations," Rarefied Gas Dynamics: 27th International Symposium, edited by D. A. Levin, I. J. Wysong, and A. L. Garcia, AIP Conference Proceedings, vol. 1333, American Institute of Physics, Melville, NY, pp. 802-807, 2011.

Webb et al., 2003: S. W. Webb and K. Pruess, "The Use of Fick's Law for Modeling Trace Gas Diffusion in Porous Media," Transport in Porous Media, vol. 51, pp. 327-341, 2003.

\* cited by examiner

Fig. 6

PARTICLE CONTROL NEAR RETICLE AND OPTICS USING SHOWERHEAD

CROSS-REFERENCE TO RELATED APPLICATIONS

This application claims the benefit under 35 U.S.C. §119 (e) from of U.S. Provisional Application No. 61/706,070 filed Sep. 26, 2012 which application is incorporated herein by reference in its entirety.

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of Contract No. DE-AC04-94AL85000 awarded by the Department of Energy.

FIELD OF THE INVENTION

The present invention relates to the field of photolithography inspection systems, particularly to extreme ultraviolet (EUV) light inspection systems, and more particularly particle free EUV inspection systems.

BACKGROUND OF THE INVENTION

Inspection tools that use EUV light cannot use a particle protection device, such as a pellicle, that may be used with inspection tools utilizing light with longer wavelengths. In EUV inspection systems, any particle on the reticle surface will cause unacceptable problems. Several particle protection mechanisms have been proposed to protect the reticle from particles generated from inspection optics that send the inspection EUV light to the reticle, generally via a central hole in a plate proximate the reticle. A second source of particles is the movable stage that moves the reticle during the inspection process.

Prior methods do not protect inspection systems from particles as small as 10 nm in diameter or they have been used in processes in which reticles are cleaned after inspections. However, with EUV inspection systems, while no cleaning is possible, particles as small as 10 nm must still be removed.

U.S. Pat. No. 7,875,864 to Sogard describes a particle protection system that combines a thermophoresis device and electrophoresis device. However, the thermophoresis device tends to heat the reticle thereby causing distortions in the reticle itself.

What is needed in the field is an apparatus, system, and/or method to protect the reticle of EUV inspection systems from particles with a diameter of 10 nm and greater.

SUMMARY OF THE INVENTION

A method and an apparatus to protect a reticle against particles and chemicals in an actinic EUV reticle inspection tool are presented. The method and apparatus utilize showerheads in the form of porous metal diffusers to provide a continual flow of clean gas. The main showerhead bathes the reticle surface to be inspected in smoothly flowing, low pressure gas, isolating it from particles coming from surrounding volumes. The secondary showerhead faces away from the reticle and toward the EUV illumination and projection optics, supplying them with purge gas while at the same time creating a buffer zone that is kept free of any particle contamination originating from those optics.

The present invention broadly comprises a particle control arrangement for an EUV illumination inspection system comprising: a thermal shroud; a first diffuser plate, the first diffuser plate having and area and an upper surface and a lower surface; a second diffuser plate, the second diffuser plate having an area, a first surface, and a second surface, wherein the first surface faces the lower surface; a reticle having an area; a photomask positioned between the reticle and the upper surface; a movable holder, the movable holder having a holder area and supporting the reticle and the photomask; a gas source, the gas source delivering a flow of gas in a channel defined by the lower surface and the first surface; a post optics box attached to the shroud and extending away from the channel and the second surface; a light tunnel having walls, the walls extending between the first diffuser plate and the second diffuser plate; and, an EUV illumination port defined by the thermal shroud. The post optics box contains an inspection lens system and the holder moves at least part of the area of the reticle over the inspection hole.

A first object of the invention is to present a EUV inspection system free from contamination of particles originating from the exterior of the system.

A second object of the invention is to supply a EUV inspection system having a flow of particle free gas that shields the reticle from particle contamination originating from the post optics box.

A third object of the invention is to demonstrate a EUV inspection system with an even flow of particle-free gas over the reticle and mask.

BRIEF DESCRIPTION OF THE SEVERAL VIEWS OF THE DRAWINGS

The nature and mode of the operation of the present invention will now be more fully described in the following detailed description of the invention taken with the accompanying drawing Figures, in which.

DETAILED DESCRIPTION OF EMBODIMENTS OF THE INVENTION

At the outset, it should be appreciated that like drawing numbers on different drawing views identify identical structural elements of the invention. It also should be appreciated that figure proportions and angles are not always to scale in order to clearly portray the attributes of the present invention.

While the present invention is described with respect to what is presently considered to be the preferred embodiments, it is understood that the invention is not limited to the disclosed embodiments. The present invention is intended to cover various modifications and equivalent arrangements included within the spirit and scope of the appended claims.

Furthermore, it is understood that this invention is not limited to the particular methodology, materials and modifications described and as such may, of course, vary. It is also understood that the terminology used herein is for the purpose of describing particular aspects only, and is not intended to limit the scope of the present invention, which is limited only by the appended claims.

Unless defined otherwise, all technical and scientific terms used herein have the same meaning as commonly understood to one of ordinary skill in the art to which this invention belongs. It should be appreciated that the term "substantially" is synonymous with terms such as "nearly", "very nearly", "about", "approximately", "around", "bordering on", "close to", "essentially", "in the neighborhood of", "in the vicinity of", etc., and such terms may be used interchangeably as appearing in the specification and claims. It should be appreciated that the term "proximate" is synonymous with terms such as "nearby", "close", "adjacent", "neighboring", "immediate", "adjoining", etc., and such terms may be used interchangeably as appearing in the specification and claims. Although any methods, devices or materials similar or equivalent to those described herein can be used in the practice or testing of the invention, the preferred methods, devices, and materials are now described.

A reticle is suspended in a pattern-side down orientation within a holder that moves the reticle back and forth across an inspection/illumination hole or "light tunnel" in a shield. The EUV light imaging and projection optics are positioned under the shield. Particles and contaminants emerge from at least three sources—the gas occupying the exterior of the holder via the edge gap separating the interior and the exterior of the shroud or housing, the gas in the optics box below the shield, and the portion of the shield exposed to the exterior of the holder and then brought into the interior portion as the stage moves. The upper and lower surfaces of the shower protection hardware are thin flat sheets of porous metal material. These porous sheets form the top and bottom diffusers or showerheads that supply the region between the shield and the reticle and the region between the inspection/illumination hole ("light tunnel") in the shield and the inspection or projection optics assembly. Essentially, the top showerhead protects the reticle from particles originating from the holder exterior and from the exposed plate surface and the bottom showerhead protects the reticle from the particles originating from the optics assembly.

Figure 1A:
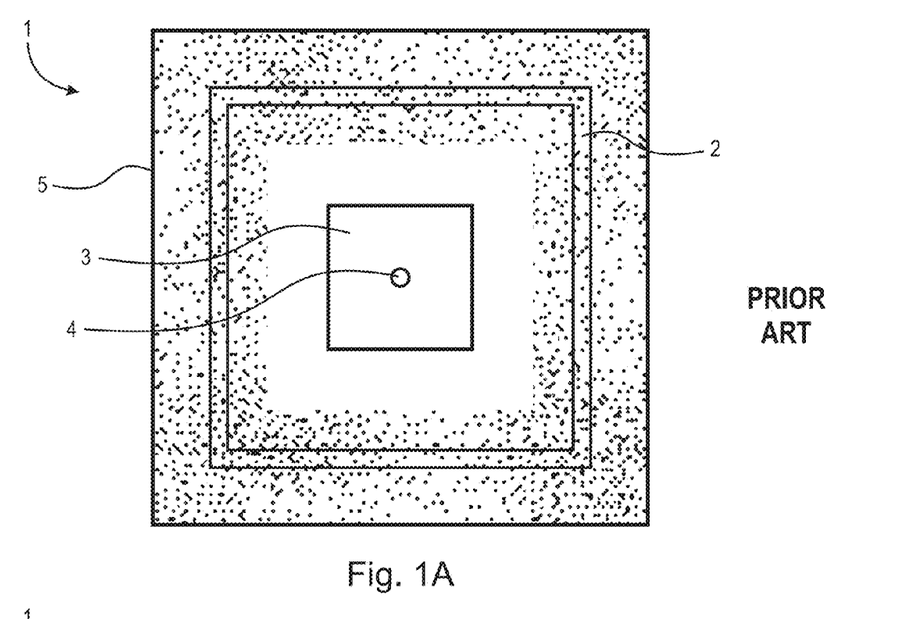
FIG. 1A is a top schematic view depicting a movable holder holding a mask over an inspection hole through which EUV illumination falls on the center of the mask in a prior art inspection system.
Figure 1B:
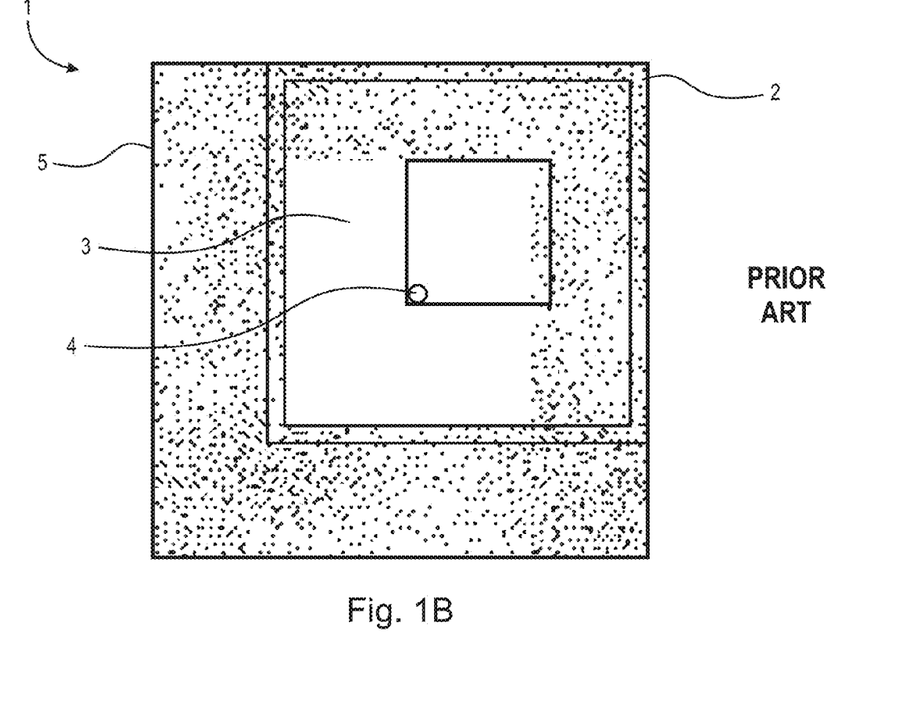
FIG. 1B is a top schematic view showing the prior art mask-holder assembly shifted to allow the lower left corner of the mask to be placed over the inspection hole to illuminate that area of the mask.

Adverting to the figures, FIGS. 1A and 1B are a top schematic views of mask-holder assembly 1 ("assembly 1") that has been exposed to particles surrounding a thermophoretic plate 5 ("plate 5") in a prior art inspection tool. In FIG. 1A, holder 2 holds reticle 3 over light tunnel 4 through which EUV illumination falls on the center of reticle 2. Holder 2 is part of the movable stage that shifts reticle 3 over light tunnel 4 so the entire area of reticle 3 can be inspected. FIG. 1B shows assembly 1 shifted so that the lower left corner of reticle 3 is over light tunnel 4 to illuminate that area of reticle 3 which is to be inspected. The shaded areas depict the areas of the plate that are exposed to particle-laden gas originating from outside the holder. These particles can deposit onto plate 5 and reticle 3 thereby compromising the inspection process.

In addition, the arrangement seen in FIGS. 1A and 1B has several disadvantages. The arrangement utilizes a relatively high gas velocity resulting in density and temperature gradients. Further, gas flow enters at an angle deviating from the normal (perpendicular) angle. Finally, the flow velocity in the holder portion of the system is dependent on the position of the reticle and holder relative to the inspection hole. Flow will be fastest near the hole and slowest at the edges providing reduced anti-particulate pressure where it is most needed.

Figure 2:
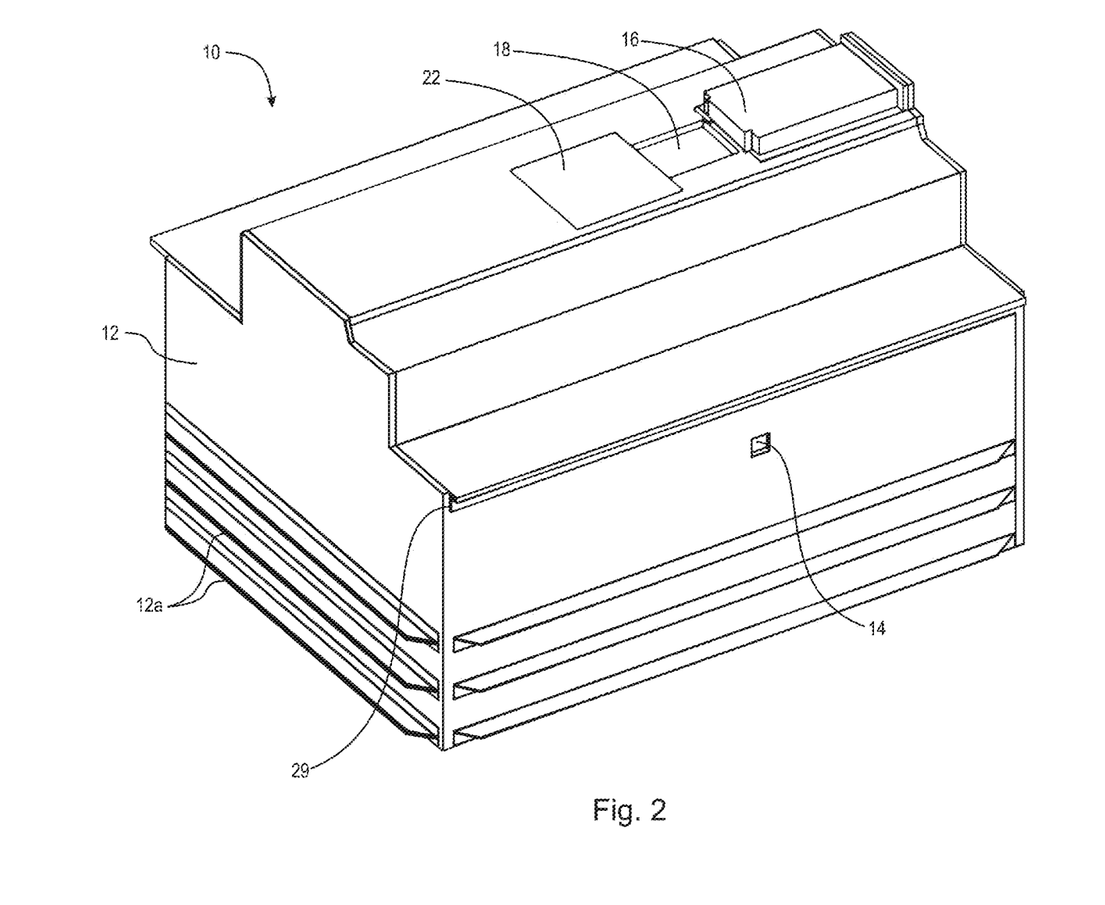
FIG. 2 is a top perspective view of the exterior of the EUV inspection system of the present invention.

FIG. 2 is a top perspective view of the exterior of EUV inspection system 10 of the present invention. Thermal shroud 12 encloses system 10 and preferably includes stiffening ribs 12a. Shroud 12 defines EUV illumination input hole 14 through which the EUV light enters the system from the EUV source. Also seen is window chamber 16 used to view the metrology column. The metrology column measures the distance of the stage relative to the optics enclosed within the shroud. In a preferred embodiment, shroud 12 holds Littrow mirror window 18 to allow fine adjustment of the light beam reflected in the projection optics. Also seen is gas diffuser plate 22 ("showerhead 22"). Thermal shroud 12 is water cooled and is contained in a vacuum to reduce or eliminate the interaction of the EUV illumination with atmospheric or other gases.

Figure 3:
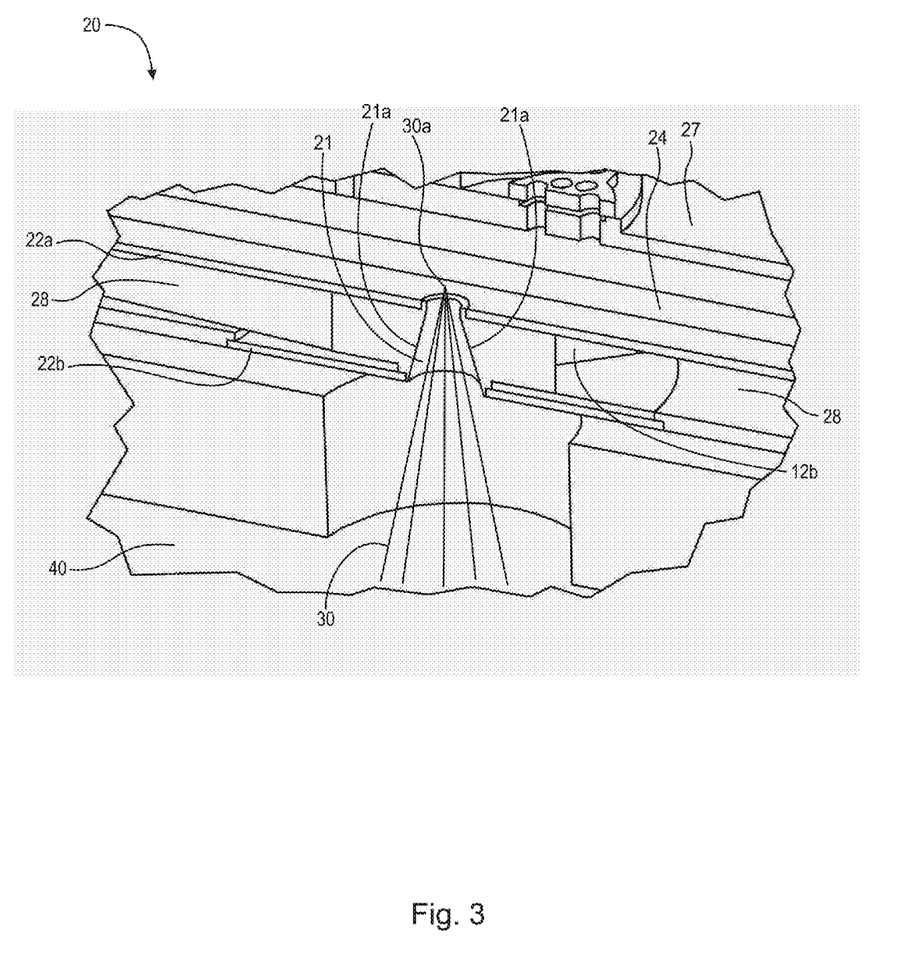
FIG. 3 is a side perspective view of the dual diffuser or dual showerhead arrangement of the present invention used to control particles in the inspection system.

FIG. 3 is a side perspective view of the dual diffuser or dual showerhead arrangement 20 used to control particles in inspection system 10. Upper diffusion plate 22a and lower diffusion plate 22b define channel 28 through which purge gas is passed as explained below. Preferably, diffuser plates 22a and 22b are fabricated from porous metal media by Mott Corp., Farmington, Ct. The metal media is fabricated by sintering small metallic particles to produce a porous matrix. Also seen is supporting rib 12b supporting upper diffuser 22a.

Reticle 24 is held and moved by holder 27. EUV light rays 30 can be seen passing through light tunnel 21 to focus on reticle 24 at focal point 30a. Pursuant to the inspection method known to those having skill in the art, rays 30 reflect back into the projection optics box 40 ("box 40") which houses the projection optics. As seen in FIG. 3, preferably light tunnel 21 has a cone shape formed by walls 21a to help focus rays 30 onto reticle 24.

In a preferred embodiment, upper diffuser 22a is square and has twice the side length of reticle 24 while the holder interior is square and three times the side length of reticle 24. This ensures the entire area of reticle 24 is always directly above upper diffuser 22a for all reticle-holder positions during inspection. In addition, upper diffuser 22a always remains within the area of interior of holder 27 for all lateral reticle-holder positions during inspection. In this way, the holder-reticle assembly part of the metrology system is always bathed in particle free gas during the inspection process.

The inner diameter of lower diffuser 22b lies outside light tunnel walls 21a and its outer diameter is the same as the diameter of the area through which the gas flows into box 40. The flow area of lower diffuser 22b is smaller than the flow area of upper diffuser 22a.

Figure 4:
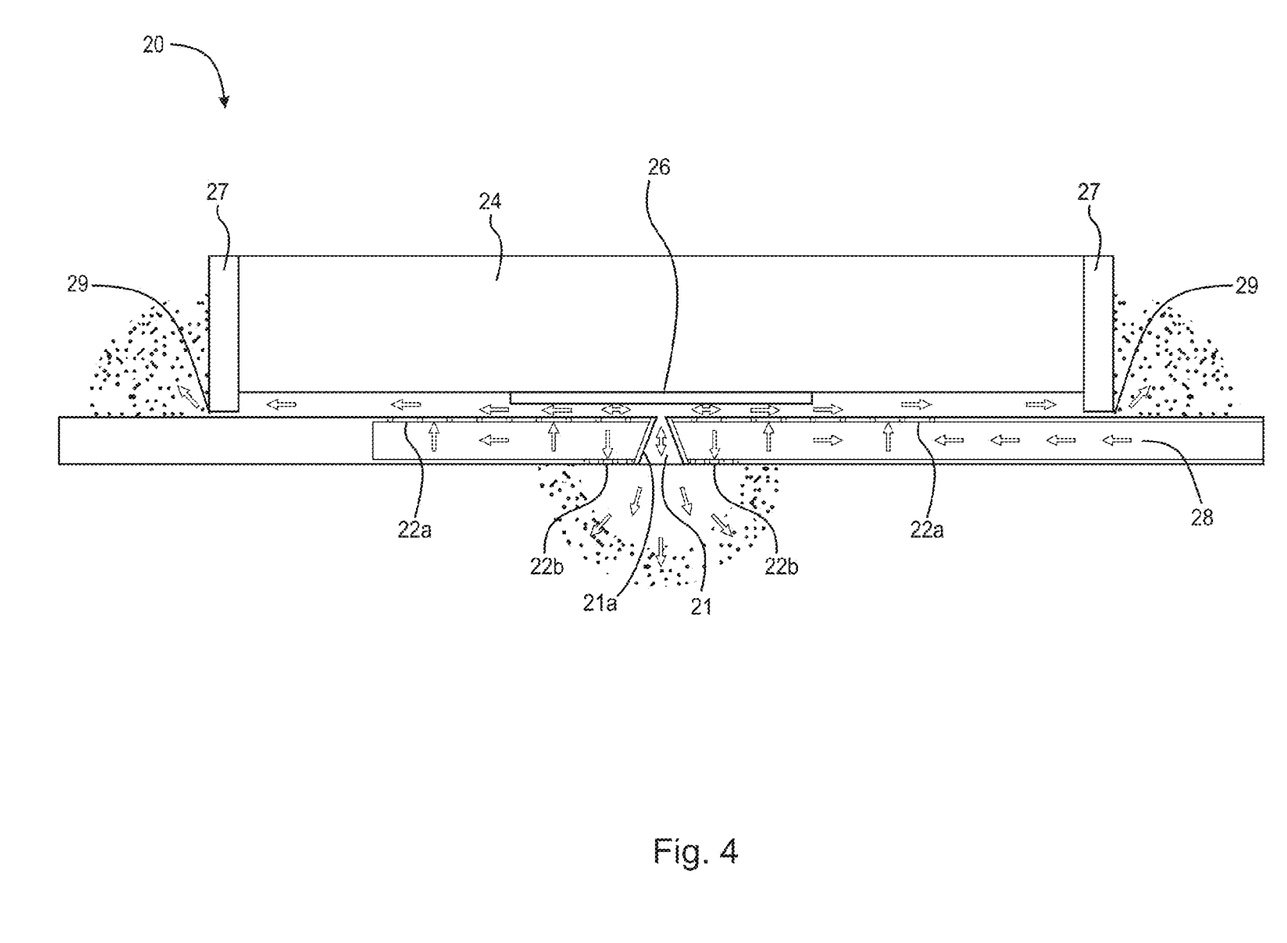
FIG. 4 is a schematic cross section of the dual showerhead arrangement demonstrating the flow of gas to form a shield protecting the reticle from particle contamination.

FIG. 4 is a schematic cross section of arrangement 20 demonstrating the flow of gas, demonstrated by the arrows, to form a shield protecting reticle 24 from particle contamination. The gas is introduced to arrangement 20 through channel 28 which acts as a plenum to distribute the gas through upper diffuser 22a and lower diffuser 22b. Preferably, the gas may be hydrogen, a noble gas such as, argon, helium, xenon, or argon, or a mixture of two or more of those gases. More preferably, the gas may be pure hydrogen which demonstrates lower reaction levels with EUV illumination compared with other gases.

After passing through upper diffuser 22a, the gas passes between the upper surface of upper diffuser 22a and mask 26 and reticle 24 before passing out gap 29. This flow creates a positive gas pressure between the interior of arrangement 20 as seen in FIG. 4, and the exterior area around holder 27 to prevent particle contamination, depicted by the shaded areas near gaps 29, from entering arrangement 20 from the exterior area.

A portion of the gas passing through upper diffuser 22a passes down light tunnel 21 to enter projection optics box 40 containing a projection lens system of the kind known to those skilled in the art. In addition, more gas enters box 40 from lower diffuser 22b on either side of light tunnel 21. Similar to the gas pressure between reticle 24-mask 26 and the upper surface of upper diffuser 22a, the gas entering box 40 from light tunnel 21 and lower diffuser 22b creates positive pressure to prevent particles from box 40 from reaching and contaminating mask 26 and reticle 24. Again, the particles from box 40 are represented by the shaded area under light tunnel 21.

Figure 5A:
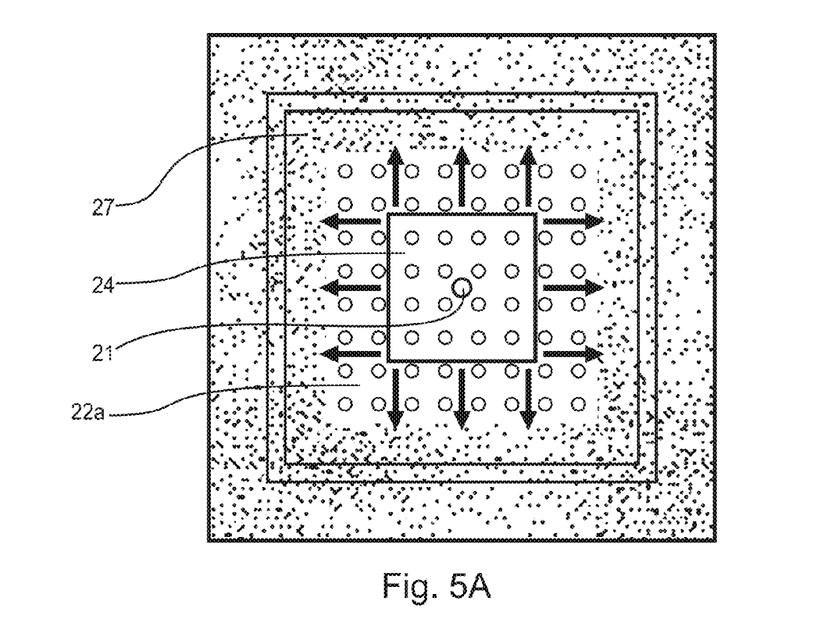
FIG. 5A is a top schematic view of the arrangement of the present invention showing the center areas of the reticle held in position over the light tunnel.
Figure 5B:
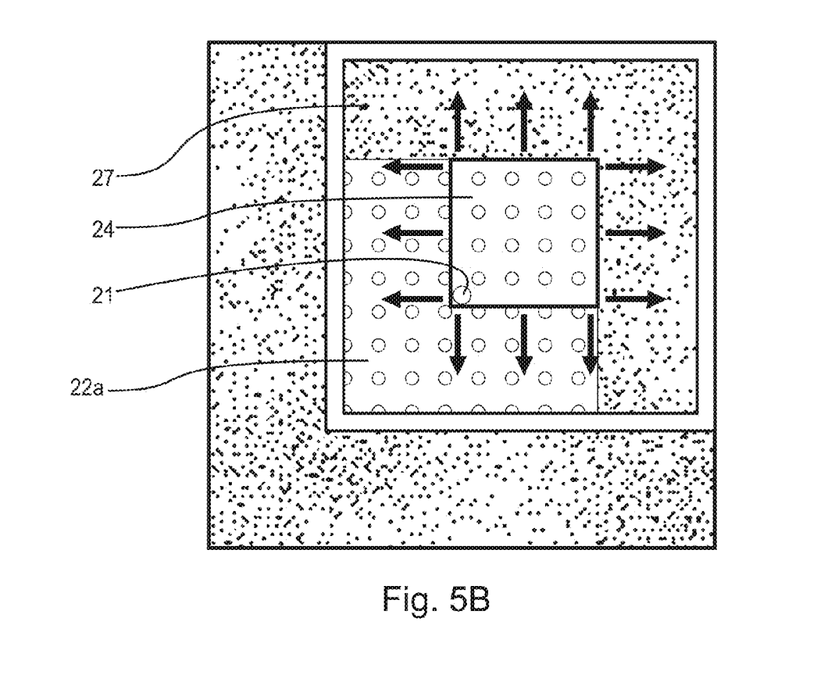
FIG. 5B is a top schematic view of the arrangement of the present invention showing the bottom left corner the reticle held in position over the light tunnel; and, FIG. 6 is a schematic representation of the EUV light path through the arrangement of the present invention.

Preferably, the gas flow in channel 26 is laminar. The laminar flow is produced by a gas flow velocity of 100 m/sec and a channel 26 width of 0.01 m. With a typical low mass density of ~$4 \times 10^{-6}$ kg/m$^3$ and a viscosity of ~$0.89 \times 10^{-5}$ Pa·s, a low Reynolds number results leading to a steady and laminar gas flow. The laminar flow creates a constant gas curtain that over time consistently shields arrangement 20 from particle contamination. Gas pressure may be less than 5 Pa FIGS. 5A and 5B are schematic top views of reticle 24 in position over upper diffuser 22a (showerhead 22a). As in FIG. 4, the arrows indicate gas flow. FIG. 5A shows the center area of reticle 24 held over light tunnel 21. Using arrangement 20, with gas flowing up from upper diffuser 22a, particle contamination, represented by the shaded area, is kept away from mask 26 and reticle 24. When holder 27 moves reticle 24 so the lower left corner is positioned over light tunnel 21 as seen in FIG. 5B, upper diffuser 22a is able to prevent particle contamination from reaching reticle 24.

Figure 6:
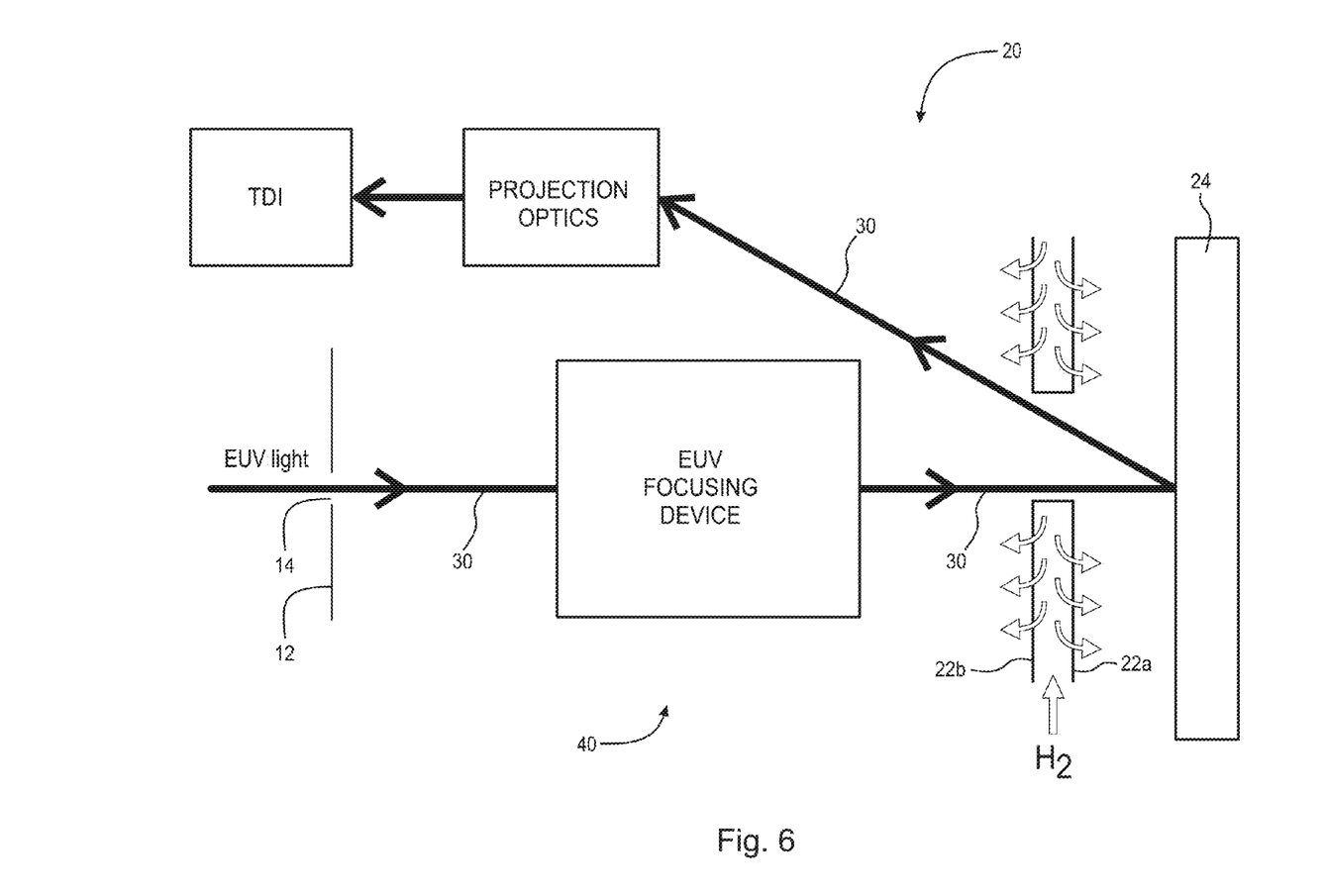

FIG. 6 is a schematic representation of the EUV light path through dual diffuser arrangement 20. EUV light 30 is emitted by a EUV light source (not seen) such as, for example an infrared laser impinging on a cylinder covered with xenon ice which acts as a EUV light source. EUV light emanates from the cylinder and is directed toward a focusing device. Rays 30 emerge from the focusing device and pass through light tunnel 21 to impinge on reticle 24 and reflect therefrom toward projection optics box 40 into the projection optics. Optionally, ray 30 will illuminate TDI (time delay integration) detector array to evaluate the inspection target.

Arrangement 20 possesses several advantages over the prior art. First, due to the large flow resistances of the porous-metal sheets used as diffusers 22a and 22b relative to channel 28 gas velocity is nearly uniform across the surface of each diffuser and nearly independent of the lateral position of holder 27 and reticle 24 relative to light tunnel 21. This also applies to loading and unloading of holder 27 when holder 27 and reticle 24 are no longer over upper diffuser 22a. Second, because the gas enters both the upper holder-reticle area and lower box 40, density and temperature gradients are small. Third, gas flow is slowest at the center and fastest at the perimeter toward gap 29 where the potential for particle contamination is stronger. In addition, channel 28 and light tunnel 21 are not exposed to particles as the gas entering channel 28 is already particle free. Finally, the metal porous diffusers fabricated by Mott are known to filter particles down to 3 nm is size.

Thus it is seen that the objects of the invention are efficiently obtained, although changes and modifications to the invention should be readily apparent to those having ordinary skill in the art, which changes would not depart from the spirit and scope of the invention as claimed.

What is claimed is:

1. A particle control arrangement for an EUV illumination inspection system comprising:
   a thermal shroud;
   a first diffuser plate, said first diffuser plate having an area and an upper surface and a lower surface;
   a second diffuser plate, said second diffuser plate having an area a first surface and a second surface, wherein said first surface faces said lower surface;
   a reticle having an area;
   a movable holder, said movable holder having a holder area and supporting said reticle;
   a gas source, said gas source delivering a flow of gas in a channel defined by said lower surface and said first surface;
   a post optics box attached to said shroud and extending away from said channel and said second surface;
   a light tunnel having walls, said walls extending between said first diffuser plate and said second diffuser plate; and,
   an EUV illumination port defined by said thermal shroud;
   wherein said post optics box contains an inspection lens system; and
   wherein said holder moves at least part of the area of said reticle over said inspection hole.

2. The particle control system as recited in claim 1 wherein said first diffuser plate and said second diffuser plate are fabricated from porous metal.

3. The particle control system as recited in claim 1 wherein said attachment to said shroud is a supporting rib.

4. The particle control system as recited in claim 1 further comprising a metrology subsystem.

5. The particle control system as recited in claim 4 wherein said metrology subsystem includes said movable reticle/mask holder.

6. The particle control system as recited in claim 4 wherein said metrology subsystem includes a Littrow mirror.

7. The particle control system as recited in claim 1 wherein the gas from said gas source is hydrogen.

8. The particle control system as recited in claim 1 wherein the gas from said gas source is a noble gas.

9. The particle control system as recited in claim 1 wherein a pressure of said gas flow is <5 Pa.

10. The particle control system as recited in claim 1 wherein said particle control system is contained within a vacuum.

11. The particle control system as recited in claim 1 wherein said shroud is water cooled.

12. The particle control system as recited in claim 1 wherein said holder is square, said square having a side length three times longer than a side length of said reticle.

13. The particle control system as recited in claim 1 wherein said first diffuser is larger than said second diffuser.

14. The particle control system as recited in claim 1 wherein said first diffuser is square and has twice the side length of said reticle.

15. The particle control system as recited in claim 14 wherein during movement of said movable holder, said area of said first diffuser remains within said holder area.

16. The particle control system as recited in claim 1 wherein said gas flow is a laminar gas flow.

* * * * *